US008986198B2

(12) United States Patent
Kobayashi et al.

(10) Patent No.: US 8,986,198 B2
(45) Date of Patent: Mar. 24, 2015

(54) IMAGE DISPLAY APPARATUS AND CAPSULE ENDOSCOPE SYSTEM

(75) Inventors: Satomi Kobayashi, Kokubunji (JP); Kei Takasugi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 254 days.

(21) Appl. No.: 13/432,193

(22) Filed: Mar. 28, 2012

(65) Prior Publication Data

US 2012/0238810 A1 Sep. 20, 2012

Related U.S. Application Data

(63) Continuation of application No. PCT/JP2011/064262, filed on Jun. 22, 2011.

(30) Foreign Application Priority Data

Sep. 28, 2010 (JP) ................................ 2010-216892

(51) Int. Cl.
*A61B 1/04* (2006.01)
*A61B 1/06* (2006.01)
(Continued)

(52) U.S. Cl.
CPC ............... *A61B 1/0005* (2013.01); *A61B 1/041* (2013.01); *A61B 5/061* (2013.01); *A61B 1/00009* (2013.01)
USPC ............ 600/117; 600/109; 600/160; 600/424

(58) Field of Classification Search
CPC .... A61B 1/041; A61B 19/564; A61B 19/566; A61B 19/568; A61B 2019/507; A61B 5/06; A61B 5/061; A61B 5/062; A61B 5/063; A61B 5/064; A61B 5/6861
USPC .......................... 600/117, 109, 118, 160, 424
See application file for complete search history.

(56) References Cited

U.S. PATENT DOCUMENTS 8,038,608 B2 * 10/2011 Shigemori et al. ............ 600/160
2006/0183993 A1 8/2006 Horn
(Continued)

FOREIGN PATENT DOCUMENTS

JP 2000-187611 A 7/2000
JP 2005-168524 A 6/2005
(Continued)

OTHER PUBLICATIONS

Decision of a Patent Grant dated Mar. 12, 2013 from corresponding Japanese Patent Application No. JP 2012-515841 together with an English-language translation.
(Continued)

*Primary Examiner* — Alireza Nia
*Assistant Examiner* — William Chou
(74) *Attorney, Agent, or Firm* — Scully, Scott, Murphy & Presser, PC

(57) ABSTRACT

An image display apparatus includes: a storage unit storing in-vivo image data and information associated with the in-vivo image data and related to a position of a capsule endoscope in a subject; an image processing unit performing image processing on the in-vivo image data stored in the storage unit; a display unit displaying an in-vivo image based on the in-vivo image data image-processed in the image processing unit; a position estimating unit estimating an intra-subject position in which an in-vivo image is captured, based on the position-related information; a control unit performing image processing in the image processing unit and position estimation processing in the position estimating unit in parallel; and a reporting unit reporting information indicating that a radiogram interpretation is possible, when image processing in the image processing unit for all the in-vivo image data is completed while processing in the position estimating unit is not completed.

9 Claims, 18 Drawing Sheets

(51) Int. Cl.

| | |
|---|---|
| ***A61B 5/05*** | (2006.01) |
| ***A61B 1/00*** | (2006.01) |
| ***A61B 5/06*** | (2006.01) |

(56) References Cited

U.S. PATENT DOCUMENTS

| | | | | |
|---|---|---|---|---|
| 2006/0202998 | A1 | 9/2006 | Hirakawa et al. | |
| 2007/0268280 | A1 | 11/2007 | Fujita et al. | |
| 2008/0306341 | A1 | 12/2008 | Fujita | |
| 2008/0312501 | A1 | 12/2008 | Hasegawa et al. | |
| 2009/0043164 | A1* | 2/2009 | Hasegawa et al. | 600/118 |
| 2010/0029236 | A1* | 2/2010 | Kimoto et al. | 455/226.2 |
| 2010/0061597 | A1 | 3/2010 | Kanda et al. | |
| 2010/0179782 | A1* | 7/2010 | Kimura et al. | 702/94 |
| 2010/0204566 | A1 | 8/2010 | Uchiyama et al. | |
| 2010/0317968 | A1* | 12/2010 | Wright et al. | 600/427 |
| 2011/0054255 | A1* | 3/2011 | Schmidt | 600/118 |
| 2011/0196201 | A1 | 8/2011 | Sato et al. | |
| 2011/0252291 | A1* | 10/2011 | Fujita et al. | 714/775 |
| 2011/0282142 | A1* | 11/2011 | Refael | 600/109 |
| 2012/0059249 | A1* | 3/2012 | Verard et al. | 600/424 |

FOREIGN PATENT DOCUMENTS

| | | | |
|---|---|---|---|
| JP | 2006-061469 | A | 3/2006 |
| JP | 2006-075301 | A | 3/2006 |
| JP | 2006-187611 | A | 7/2006 |
| JP | 2006-314626 | A | 11/2006 |
| JP | 2007-608 | A | 1/2007 |
| JP | 2007-283001 | A | 11/2007 |
| JP | 2008-100075 | A | 5/2008 |
| JP | 2008-301953 | A | 12/2008 |
| WO | WO 2008/149674 | A1 | 12/2008 |
| WO | WO 2009/019916 | A1 | 2/2009 |
| WO | WO 2010/103868 | A1 | 9/2010 |

OTHER PUBLICATIONS

International Search Report PCT/JP2011/064262 dated Aug. 9, 2011.

* cited by examiner

100

120

170

175

| ID | NAME | TRANS-FER | IMAGE PROC-ESSING | POSI-TION ESTI-MATION | TRAJEC-TORY CREA-TION | INITIAL-IZATION | OBSERV-ATION IS POSSIBLE | POSI-TION DISPLAY | TRAJEC-TORY DISPLAY |
|---|---|---|---|---|---|---|---|---|---|
| 12345 | OO OO | | | | | | | | |

| ID | NAME | TRANSFER | IMAGE PROCESSING | POSITION ESTIMATION | TRAJECTORY CREATION | INITIALIZATION | OBSERVATION IS POSSIBLE | POSITION DISPLAY | TRAJECTORY DISPLAY |
|---|---|---|---|---|---|---|---|---|---|
| ***** | **** | | | | | | | | |
| ***** | ******** | | | | | | | | |
| ***** | ****** | | | | | | | | |
| ***** | **** | | | | | | | | |
| ***** | ****** | | | | | | | | |
| ***** | ****** | | | | | | | | |

IMAGE DISPLAY APPARATUS AND CAPSULE ENDOSCOPE SYSTEM

CROSS-REFERENCE TO RELATED APPLICATIONS

This application is a continuation of PCT international application Ser. No. PCT/JP2011/064262 filed on Jun. 22, 2011 which designates the United States, incorporated herein by reference, and which claims the benefit of priorities from Japanese Patent Application No. 2010-216892, filed on Sep. 28, 2010 incorporated herein by reference.

BACKGROUND OF THE INVENTION

1. Field of the Invention

The present invention relates to an image display apparatus that displays an in-vivo image obtained by a capsule endoscope inserted in a subject body, and a capsule endoscope system.

2. Description of the Related Art

Conventionally, in an examination of a subject using a capsule endoscope that is inserted in a subject body and captures an image inside the body, an in-vivo image group obtained by the capsule endoscope is observed in a pseudo moving image or a still image list to select what has an abnormal observation. This operation is called "observation."

When an abnormal observation is found, in order to identify in which portion (i.e. which organ) in the subject body it is found, a method of estimating the position of each in-vivo image captured in the subject and a method of creating the trajectory of the capsule endoscope in the subject have also been proposed (for example, see Japanese Laid-open Patent Publication No. 2006-75301, Japanese Laid-open Patent Publication No. 2007-283001 and Japanese Laid-open Patent Publication No. 2008-100075).

SUMMARY OF THE INVENTION

An image display apparatus according to an aspect of the present invention displays an image based on in-vivo image data obtained from a capsule endoscope that captures an in-vivo image of a subject via a receiving apparatus that performs wireless communication with the capsule endoscope, the apparatus including: a storage unit configured to store the in-vivo image data and information that is associated with the in-vivo image data and related to a position of the capsule endoscope in the subject; an image processing unit configured to perform image processing on the in-vivo image data stored in the storage unit; a display unit configured to display an in-vivo image based on the in-vivo image data on which the image processing is performed in the image processing unit; a position estimating unit configured to estimate a position in the subject in which an in-vivo image is captured, based on the information related to the position; a control unit configured to perform image processing in the image processing unit and position estimation processing in the position estimating unit in parallel; and a reporting unit configured to report information that an observation is possible, when the image processing in the image processing unit for all the in-vivo image data is completed while processing in the position estimating unit is not completed.

A capsule endoscope system according to another aspect of the present invention includes: a capsule endoscope that is inserted in a subject body to capture an image and generates in-vivo image data indicating an in-vivo image of the subject; a receiving apparatus that receives the in-vivo image data generated by the capsule endoscope by wireless communication; and an image display apparatus that displays an image based on the in-vivo image data obtained via the receiving apparatus, wherein the image display apparatus includes: a storage unit configured to store the in-vivo image data and information that is associated with the in-vivo image data and related to a position of the capsule endoscope in the subject; an image processing unit configured to perform image processing on the in-vivo image data stored in the storage unit; a display unit configured to display an in-vivo image based on the in-vivo image data on which the image processing is performed in the image processing unit; a position estimating unit configured to estimate a position in the subject in which an in-vivo image is captured, based on the information related to the position; a control unit configured to perform image processing in the image processing unit and position estimation processing in the position estimating unit in parallel; and reporting unit configured to report information that an observation is possible, when the image processing in the image processing unit for all the in-vivo image data is completed while processing in the position estimating unit is not completed.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 20 is a schematic diagram illustrating one example of a processing status bar displayed in a case where data processing related to a plurality of patients is performed in parallel.

DETAILED DESCRIPTION OF THE PREFERRED EMBODIMENTS

In the following, an image display apparatus and a capsule endoscope system according to an embodiment of the present invention will be described with reference to the drawings. Here, in the following description, although a system including a capsule endoscope which is inserted in a subject body and captures an in-vivo image is shown as an example, the present invention is not limited to this embodiment.

Embodiment

Figure 1:
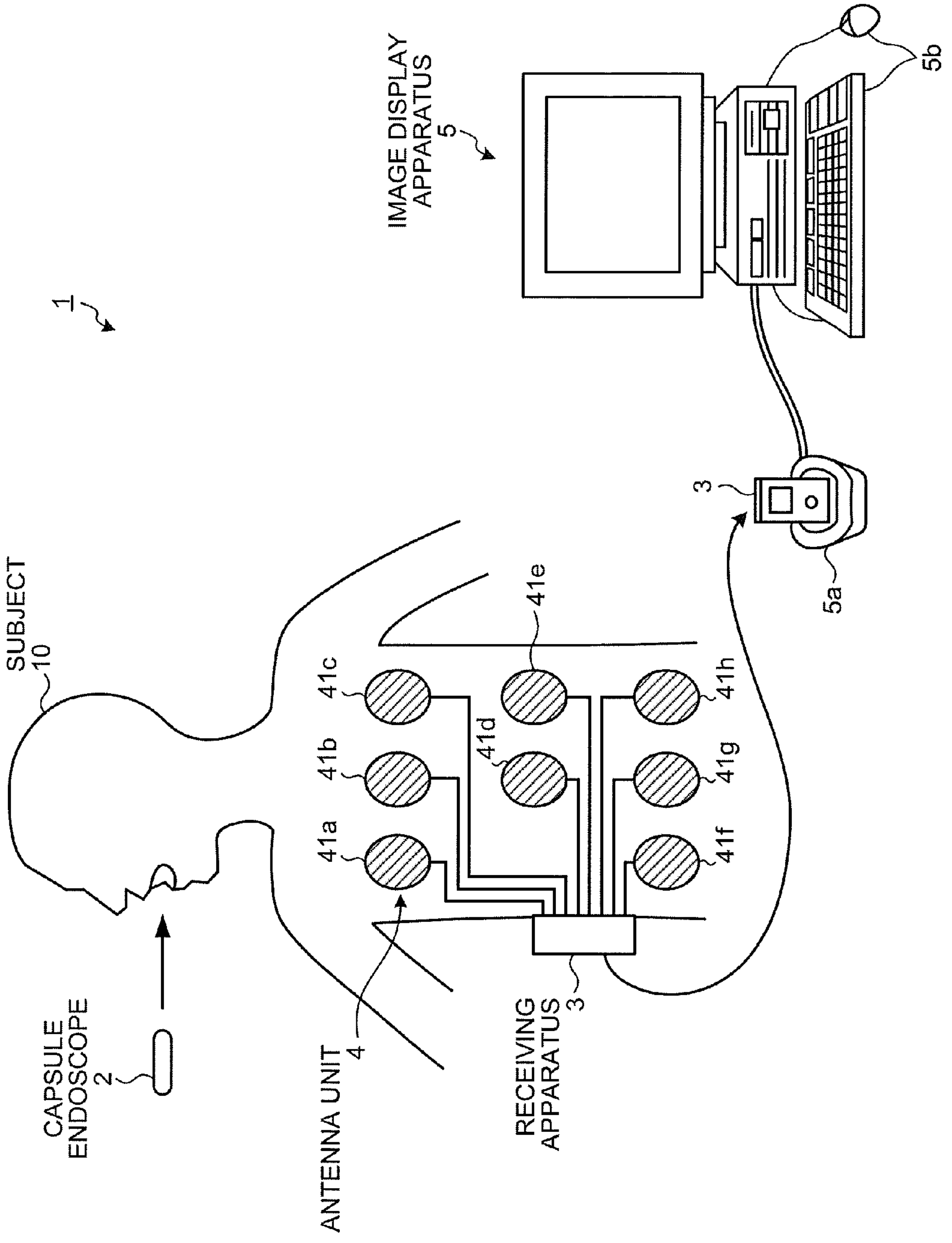
FIG. 1 is a diagram illustrating a schematic configuration of a capsule endoscope system according to an embodiment of the present invention.

FIG. 1 is a diagram illustrating a schematic configuration of a capsule endoscope system. This capsule endoscope system 1 includes: a capsule endoscope 2 that is inserted in the body of a subject 10 to capture an image and transmits image data of an in-vivo image by radio to a receiving apparatus 3; the receiving apparatus 3 that receives the in-vivo image data transmitted by radio from the capsule endoscope 2; and an image display apparatus 5 that displays an in-vivo image based on the in-vivo image data received by the receiving apparatus 3.

After the capsule endoscope 2 is swallowed via the mouse of the subject 10, the capsule endoscope 2 generates in-vivo image data by moving inside the organs of the subject 10 by organ peristaltic motion or the like and performing predetermined signal processing on image signals obtained by sequentially capturing images inside the body of the subject 10 at predetermined time intervals (for example, at 0.5 second intervals). Also, the capsule endoscope 2 sequentially transmits generated in-vivo image data by radio to the receiving apparatus 3 every time an in-vivo image of the subject 10 is captured. The capsule endoscope 2 holds assigned identification information (for example, serial number) to identify the individual of the capsule endoscope, and transmits this identification information by radio together with the in-vivo image data.

The receiving apparatus 3 has an antenna unit 4 having a plurality of receiving antennas 41*a* to 41*h*. The receiving antennas 41*a* to 41*h* are each obtained using a loop antenna, for example, and arranged in predetermined positions on the body surface of the subject 10 (for example, positions corresponding to the organs inside the subject 10 which are pass routes of the capsule endoscope 2). Here, arrangement of the receiving antennas 41*a* to 41*h* may be arbitrarily changed according to purposes such as an examination or a diagnosis. Also, it is not necessary to interpret that the number of antennas provided in the antenna unit 4 is limited to eight as illustrated by the receiving antennas 41*a* to 41*h*, and it may be less or greater than eight.

While the capsule endoscope 2 captures an image (for example, from the time it is inserted via the mouth of the subject 10 until it passes the gastrointestinal tract and is excreted), the receiving apparatus 3 is held by the subject 10 and receives the in-vivo image data transmitted by radio from the capsule endoscope 2 via the antenna unit 4. The receiving apparatus 3 stores the received in-vivo image data in a built-in memory. Also, the receiving apparatus 3 associates reception strength information of the receiving antennas 41*a* to 41*h* upon receiving in-vivo images or time information indicating the reception time, with the above in-vivo image data to be stored in the above memory. Here, these reception strength information and time information are used in the image display apparatus 5 as information related to a position of the capsule endoscope 2. After the capsule endoscope 2 finishes capturing images, the receiving apparatus 3 is removed from the subject 10 and connected to the image display apparatus 5 for transferring (or downloading) information such as in-vivo image data.

The image display apparatus 5 is obtained by a workstation or a personal computer having a display unit such as a CRT display and a liquid crystal display, and displays in-vivo images based on the in-vivo image data obtained via the receiving apparatus 3. Also, an operation input device 5*b* such as a keyboard and a mouse are connected to the image display apparatus 5. Alternatively, as the operation input device 5*b*, a touch panel overlapping the display unit may be used. By operating these operation input devices 5*b* and performing a observation of the in-vivo images of the subject 10 sequentially displayed on the image display apparatus 5, the user (observer) observes (examines) the body parts (such as an esophagus, a stomach, a small intestine and a large intestine) inside the subject 10 and, based on this, diagnoses the subject 10.

Further, the image display apparatus 5 has, for example, a USB (universal serial bus) port and is connected to a cradle 5*a* via this USB port. The cradle 5*a* is a reading apparatus that reads in-vivo image data from a memory of the receiving apparatus 3. When the receiving apparatus 3 is attached to the cradle 5*a*, the receiving apparatus 3 is electrically connected to the image display apparatus 5 so that the in-vivo image data stored in the memory of the receiving apparatus 3, and associated information such as the reception strength information and time information associated with the in-vivo image data and the identification information of the capsule endoscope 2 are transferred to the image display apparatus 5. The image display apparatus 5 obtains a series of in-vivo image data related to the subject 10 and its associated information in this way, and, by further performing processing described later, displays in-vivo images. Here, the image display apparatus 5 may be connected to an output apparatus such as a printer to output the in-vivo images to this output apparatus.

Also, the image display apparatus 5 can obtain in-vivo image data captured by the capsule endoscope 2 in various methods in addition to the one explained above. For example, in the receiving apparatus 3, instead of the built-in memory, it may be possible to use a memory that can be removed from the receiving apparatus 3 such as a USB memory and a compact flash (registered trademark). In this case, after the in-vivo image data from the capsule endoscope 2 is stored in the memory, it is required to remove only this memory from the receiving apparatus 3 and insert it into, for example, the USB port of the image display apparatus 5. Alternatively, it may be possible to provide a communication function with an external device to the image display apparatus 5 and obtain the in-vivo image data from the receiving apparatus 3 by wired or wireless communication.

Figure 2:
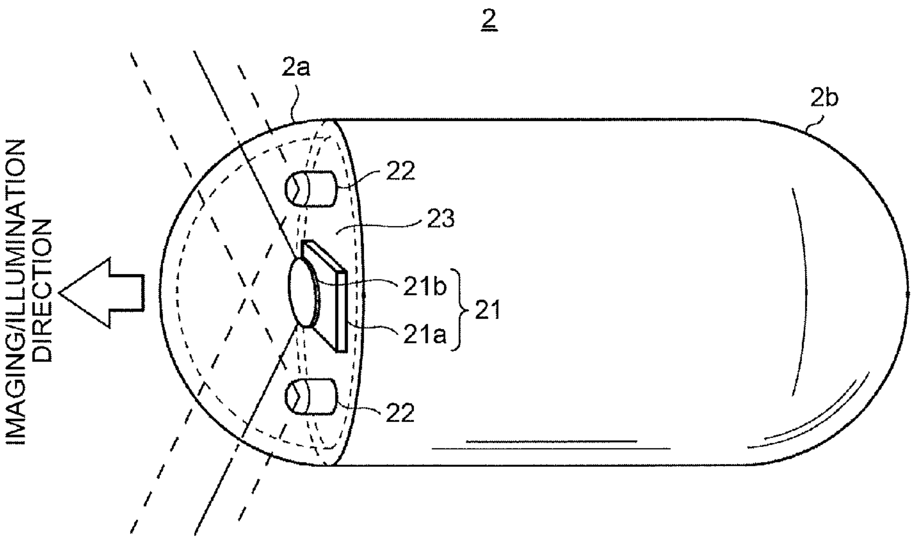
FIG. 2 is a diagram illustrating a schematic configuration of the capsule endoscope illustrated in FIG. 1.

Next, each apparatus forming the capsule endoscope system 1 will be described in detail. FIG. 2 is a schematic diagram illustrating one configuration example of the capsule endoscope 2. Also, FIG. 3 is a block diagram illustrating configurations of the capsule endoscope 2 and the receiving apparatus 3.

As illustrated in FIG. 2, the capsule endoscope 2 is contained in a capsule container (casing) configured with: a container **2*b* having a substantially-cylindrical shape or a semielliptical shape that has a hemispherical dome shape on one edge and an opening on the other edge; and a hemispherical optical dome 2*a* that is attached to the opening of the container 2*b* to seal the container 2*b* in a watertight manner. This capsule container (2*a*, 2*b*) has a size so as to be swallowed by the subject 10, for example. Here, in the present embodiment, at least the optical dome 2*a*** is formed by a transparent material.

Figure 3:
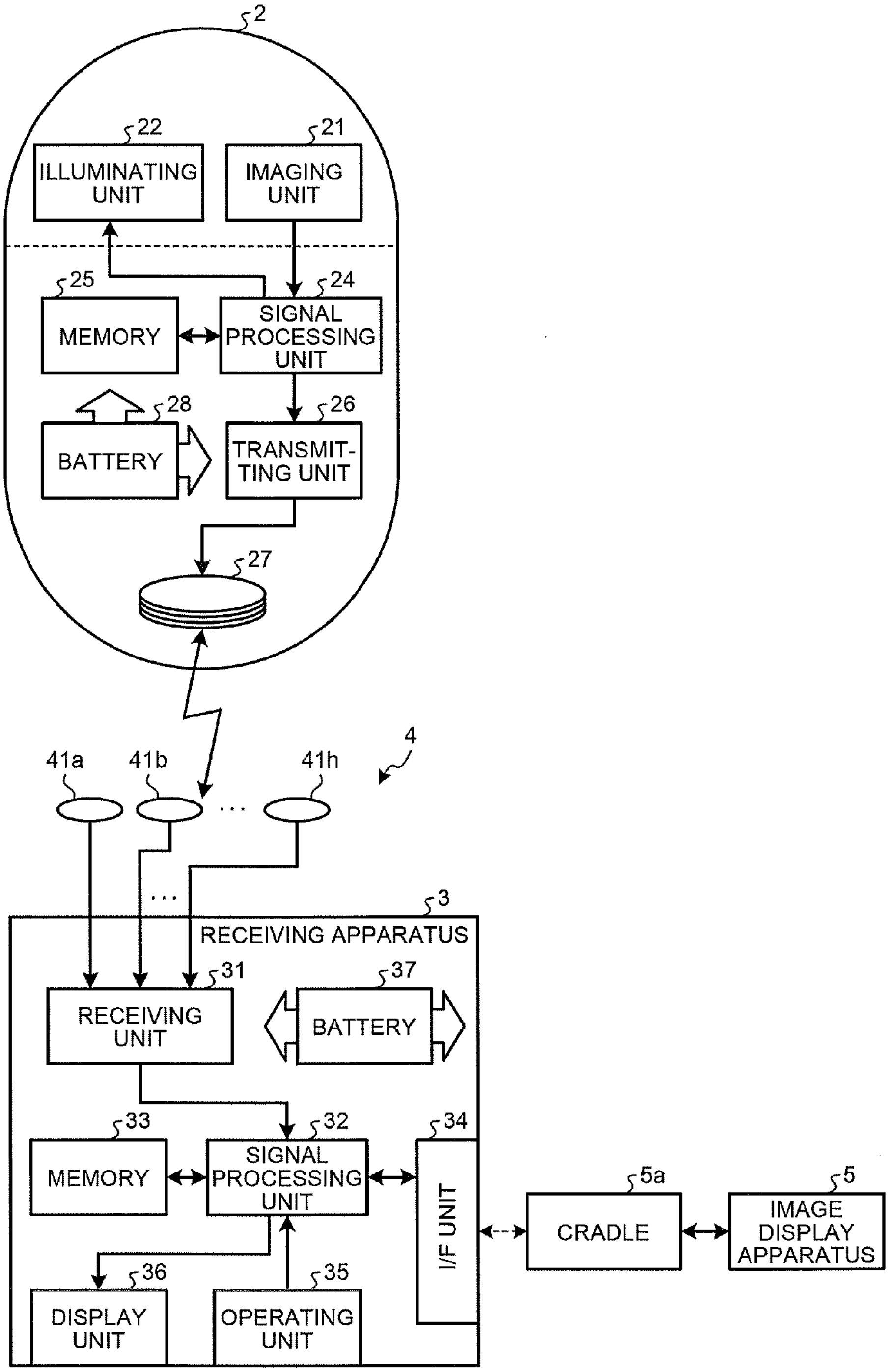
FIG. 3 is a block diagram illustrating configurations of the capsule endoscope and the receiving apparatus illustrated in FIG. 1.

Also, as illustrated in FIGS. 2 and 3, the capsule endoscope 2 has an imaging unit 21 that captures an image inside the subject 10, illuminating units 22 that illuminate the inside of the subject 10 upon capturing an image, a circuit substrate 23 on which a driving circuit or the like for driving the imaging unit 21 and the illuminating units 22 is formed, a signal processing unit 24, a memory 25, a transmitting unit 26, an antenna 27 and a battery 28.

For example, the imaging unit 21 includes an imaging element **21*a* such as a CCD and CMOS for generating image data of an intra-subject image from an optical image formed on a light-receiving surface, and an optical system 21*b* such as a field lens provided on the light-receiving surface side of the imaging element 21*a*. Also, the illuminating unit 22 is obtained by, for example, an LED (light emitting diode) that emits light to the inside of the subject 10 upon capturing an image. The imaging element 21*a*, the optical system 21*b* and the illuminating units 22 are mounted on the circuit substrate 23**.

A driving circuit of the imaging unit 21 operates under control of the signal processing unit 24 described later, generates an image signal representing an intra-subject image periodically (for example, two images per second), and inputs it in the signal processing unit 24. Here, in the following, an explanation will be given with the assumption that the imaging unit 21 and the illuminating unit 22 contain respective driving circuits.

The circuit substrate 23 on which the imaging unit 21 and the illuminating units 22 are mounted is arranged on the side of the optical dome **2*a* in the capsule container (2*a*, 2*b*) in which the light-receiving surface of the imaging element 21*a* and the light emission direction of the illuminating unit 22 are directed to the inside of the subject 10 via the optical dome 2*a*. Therefore, as illustrated in FIG. 2, the imaging direction of the imaging unit 21 and the illumination direction of the illuminating unit 22 are directed to the outside of the capsule endoscope 2 via the optical dome 2*a*. By this means, it is possible to capture an image inside the subject 10 by the imaging unit 21 while illuminating the inside of the subject 10 by the illuminating unit 22**.

The signal processing unit 24 controls each unit in the capsule endoscope 2, generates digital in-vivo image data by A/D conversion of the image signal output from the imaging unit 21 and further performs predetermined signal processing. The memory 25 temporarily stores various operations performed by the signal processing unit 24 and in-vivo image data that has been subjected to signal processing in the signal processing unit 24. The transmitting unit 26 and the antenna 27 superposes the in-vivo image data stored in the memory 25 and the identification information of the capsule endoscope 2 on a radio signal and transmit to the outside. The battery 28 supplies an electrical power to each unit in the capsule endoscope 2. Here, it is assumed that the battery 28 contains a power circuit configured to, for example, boost an electrical power supplied from a primary battery or a secondary battery such as a button battery.

On the other hand, the receiving apparatus 3 has a receiving unit 31, a signal processing unit 32, a memory 33, an interface (I/F) unit 34, an operating unit 35, a display unit 36 and a battery 37. The receiving unit 31 receives the in-vivo image data transmitted by radio from the capsule endoscope 2, via the receiving antennas **41*a* to 41*h*. The signal processing unit 32 controls each unit in the receiving apparatus 3 and performs predetermined signal processing on the in-vivo image data received in the receiving unit 31. The memory 33 stores various operations performed by the signal processing unit 32 and in-vivo image data and its related information (such as reception strength information and time information) that has been subjected to signal processing in the signal processing unit 32. The interface unit 34 transmits the image data stored in the memory 33 to the image display apparatus 5 via the cradle 5*a*. The operating unit 35 inputs various operation instructions or settings to the receiving apparatus 3 by the user. The display unit 36 provides or displays various kinds of information to the user. The battery 37 supplies an electrical power to each unit in the receiving apparatus 3**.

Figure 4:
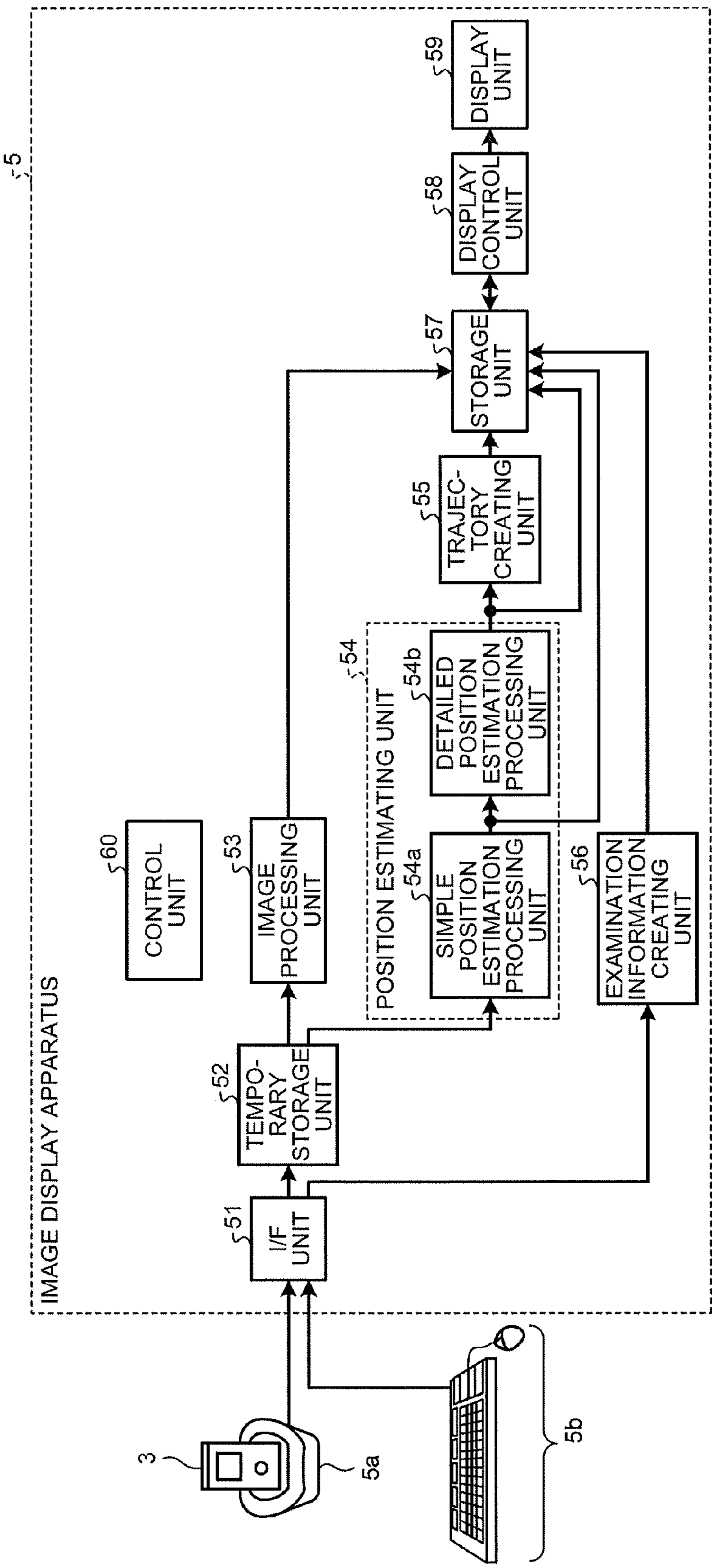
FIG. 4 is a block diagram illustrating a configuration of the image display apparatus illustrated in FIG. 1.

FIG. 4 is a block diagram illustrating a configuration of the image display apparatus 5. As illustrated in FIG. 4, the image display apparatus 5 has an interface (I/F) unit 51, a temporary storage unit 52, an image processing unit 53, a position estimating unit 54, a trajectory creating unit 55, an examination information creating unit 56, a storage unit 57, a display control unit 58, a display unit 59 and a control unit 60.

The interface unit 51 receives the in-vivo image data and its related information input via the cradle **5*a* and various orders and information input via the operation input device 5*b***.

The temporary storage unit 52 is obtained by a volatile memory such as a DRAM and a SRAM, and temporarily stores the in-vivo image data input from the receiving apparatus 3 via the interface unit 51. Alternatively, instead of the temporary storage unit 52, it may be possible to provide a storage medium such as a HDD (hard disk drive), an MO (magnetoptical disc), a CD-R and a DVD-R, and a driving apparatus that drives the storage medium, to temporarily store the in-vivo image data input from the interface unit 51 in the above storage medium.

The image processing unit 53 performs various kinds of image processing such as white balance processing, demosaicing, color conversion, density conversion (such as gamma conversion), smoothing (such as noise rejection), sharping (such as edge reinforcement) and image recognition on the in-vivo image data stored in the temporary storage unit 52. To be more specific, the image recognition processing includes: detecting a feature image area of, for example, a neoplastic, vascular or hemorrhagic lesion area; identifying an organ; and computing an average color to detect a bleeding region.

The position estimating unit 54 performs position estimation processing for estimating a position of the capsule endoscope 2 upon capturing an in-vivo image (i.e. position of a region captured in the in-vivo image). The processing in the position estimating unit 54 includes simple position estimation processing and detailed position estimation processing for estimating a position of the capsule endoscope 2 in two stages.

A simple position estimation processing unit 54*a* and a detailed position estimation processing unit 54*b* perform position estimation processing based on the reception strength information and time information stored in the temporary storage unit 52. To be more specific, the simple position estimation processing unit 54*a* and the detailed position estimation processing unit 54*b* obtain the reception strengths of the receiving antennas 41*a* to 41*h* associated with in-vivo image data received at given time from the temporary storage unit 52 and extract spherical areas with the antennas 41*a* to 41*h* being centers and the distance corresponding to the reception strengths being radiuses. Here, when the reception strength becomes weaker, this radius becomes large. A position in which these areas are crossed is estimated as a position of the capsule endoscope 2 at that time, that is, a position inside the subject 10 indicated by the in-vivo image. The simple position estimation processing unit 54*a* performs such position estimation processing at predetermined sampling density (first time). After that, the detailed position estimation processing unit 54*b* makes the sampling density higher than that of the first position estimation processing and performs second position estimation processing. Information (estimation position information) indicating positions estimated by the simple position estimation processing unit 54*a* and the detailed position estimation processing unit 54*b* is associated with time information and stored in the storage unit 57. Here, the position estimation processing needs not be necessarily performed in time series for all in-vivo images.

The trajectory creating unit 55 performs trajectory creation processing for creating the trajectory from the time the capsule endoscope 2 is inserted in the subject 10 until it is excreted. To be more specific, the trajectory creating unit 55 extracts two temporally-adjacent points from multiple estimated positions of the capsule endoscope 2, based on the estimation position information obtained by the position estimating unit 54, and if the distance between these two points is equal to or less than a predetermined value, connects these two points. In this way, by sequentially connecting estimated positions, the trajectory creating unit 55 calculates a total trajectory.

Here, regarding specific methods of the position estimation processing and the trajectory creation processing, in addition to the above, various known methods are applicable.

The examination information creating unit 56 creates information related to the examination based on the information input via the operation input device 5*b*. To be more specific, it includes patient information for identifying the subject 10 that is a patient (such as ID, name, gender, age and birth date) and examination information for identifying examination content for the subject 10 (such as hospital name, name of capsule administration doctor (nurse), capsule administration date, data acquisition date, serial number of the capsule endoscope 2 and serial number of the receiving apparatus 3). Here, this examination information may be created in advance before the in-vivo image data is transferred from the receiving apparatus 3 or may be created after the in-vivo image data is transferred.

In addition to various processing programs performed in the image display apparatus 5, the storage unit 57 stores the in-vivo image data that has been subjected to image processing in the image processing unit 53, the estimation position information obtained in the position estimating unit 54, the trajectory created by the trajectory creating unit 55, the examination information created in the examination information creating unit 56 and the like. The storage unit 57 is obtained by a semiconductor memory such as a flash memory, a RAM (random access memory) and a ROM (read only memory), a storage medium such as an HDD (hard disk drive), MO (magnetoptical disc), a CD-R and a DVD-R, and a driving apparatus that drives the storage medium.

The display control unit 58 controls the display unit 59 so as to display the in-vivo image and various kinds of information in a predetermined form. Also, in the present embodiment, the display control unit 58 functions as a reporting unit for reporting, to the user, the status of the image display apparatus 5 and the processing status in the units of the image processing unit 53 to the trajectory creating unit 55, by screen display.

The display unit 59 is obtained by a CRT display or a liquid crystal display, and, under control of the display control unit 58, displays a observation screen including the in-vivo images of the subject 10 and various kinds of information.

The control unit 60 controls the operation of the units ranging between the temporary storage unit 52 and the display unit 59. For example, the control unit 60 controls the image processing unit 53, the position estimating unit 54 and the trajectory creating unit 55 so as to perform image processing of the in-vivo image data and position estimation processing and trajectory creation processing of the capsule endoscope 2 in parallel.

Figure 5:
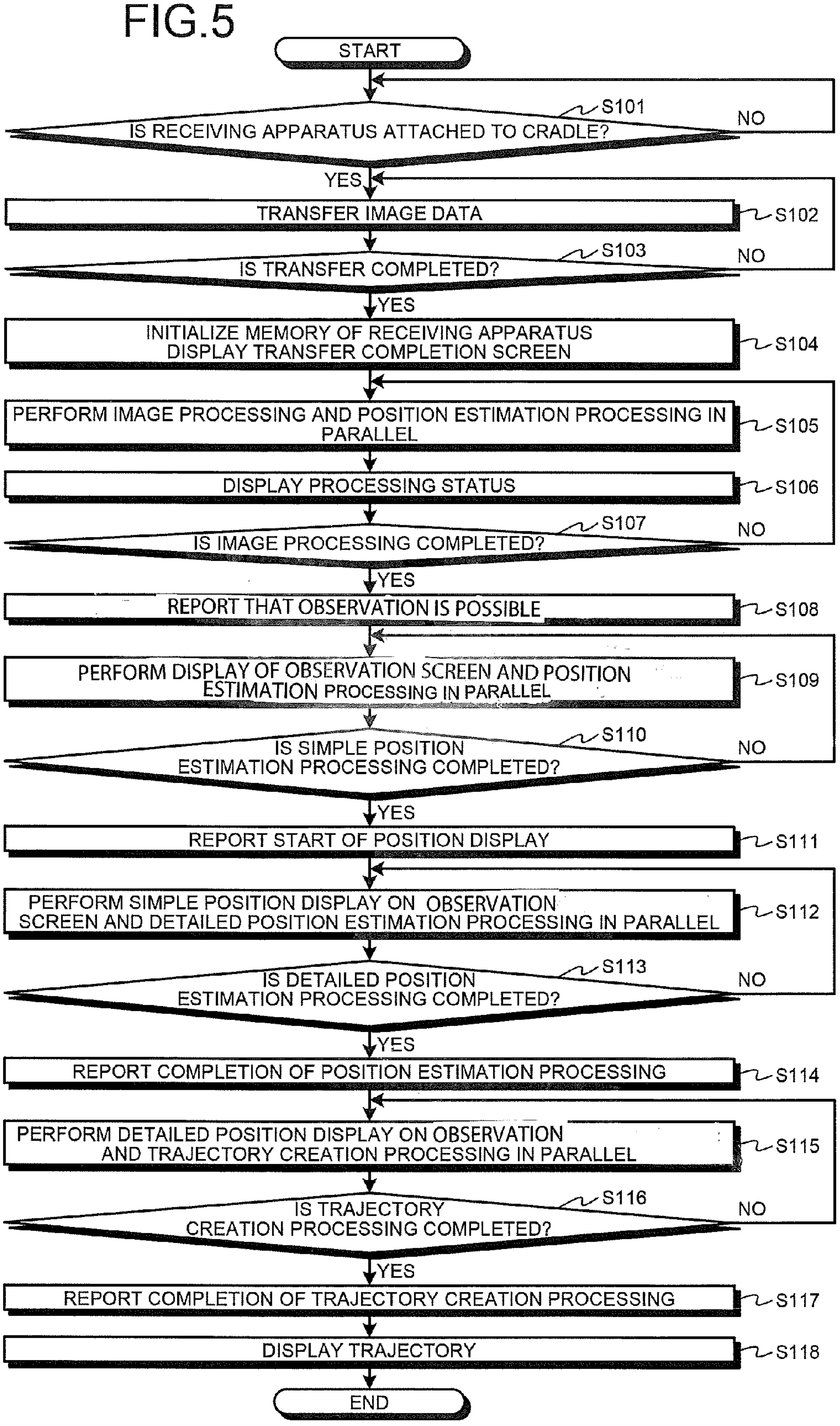
FIG. 5 is a flowchart illustrating operations of the image display apparatus illustrated in FIG. 4.

Next, operations of the image display apparatus 5 will be described with reference to FIG. 5. FIG. 5 is a flowchart illustrating operations of the image display apparatus 5.

In step S101, when the receiving apparatus 3 is attached to the cradle 5*a* (step S101: Yes), a transfer of the in-vivo image data and its related information stored in the memory of the receiving apparatus 3 to the image display apparatus 5 is started (step S102). The transferred in-vivo image data and the like are stored in the temporary storage unit 52. Here, if the receiving apparatus 3 is not attached to the cradle 5*a* (step S101: No), the image display apparatus 5 waits until the receiving apparatus 3 is attached.

Figure 6:
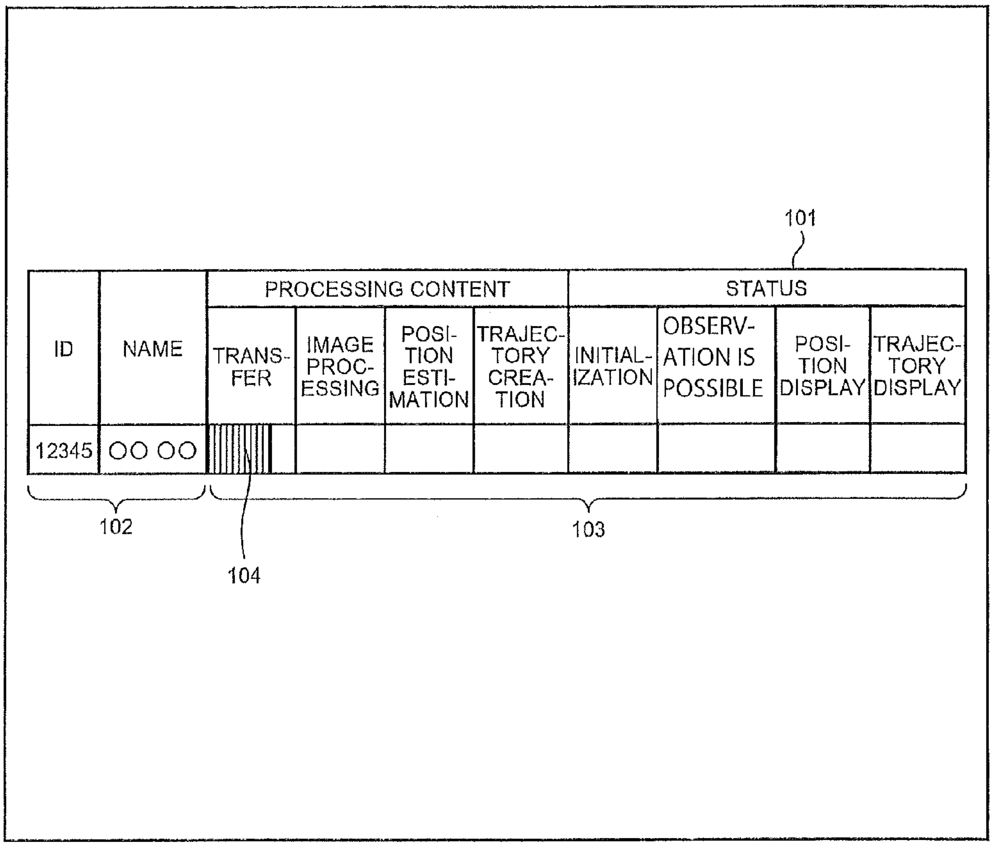
FIG. 6 is a schematic diagram illustrating one example of a transfer status display screen displayed on a display unit while in-vivo image data is transferred.

FIG. 6 is a schematic diagram illustrating one example of a screen displayed on the display unit 59 while in-vivo image data is transferred. During this, the display control unit 58 may control the display unit 59 so as to display a transfer status display screen 100 illustrated in FIG. 6, for example. This transfer status display screen 100 includes a processing status bar 101 indicating an execution status of the current processing. The processing status bar 101 provides a patient information column 102 for showing the ID and the name of a patient corresponding to the currently-transferred in-vivo image data, and a processing status display column 103 indicating the currently-executed processing content and status. Among these, in a case where the examination information creating unit 56 creates examination information in advance, the patient information column 102 is filled out by extracting corresponding examination information from the storage unit 57 based on identification information of the currently-transferred capsule endoscope 2. Also, in each of the processing status display columns 103, the processing progress status is displayed by a progress bar 104. Here, instead of the progress bar 104, it may be possible to express it by letters with a numerical value like "70% completed." Such processing continues until the transfer of image data is completed (step S103: No, S102).

Figure 7:
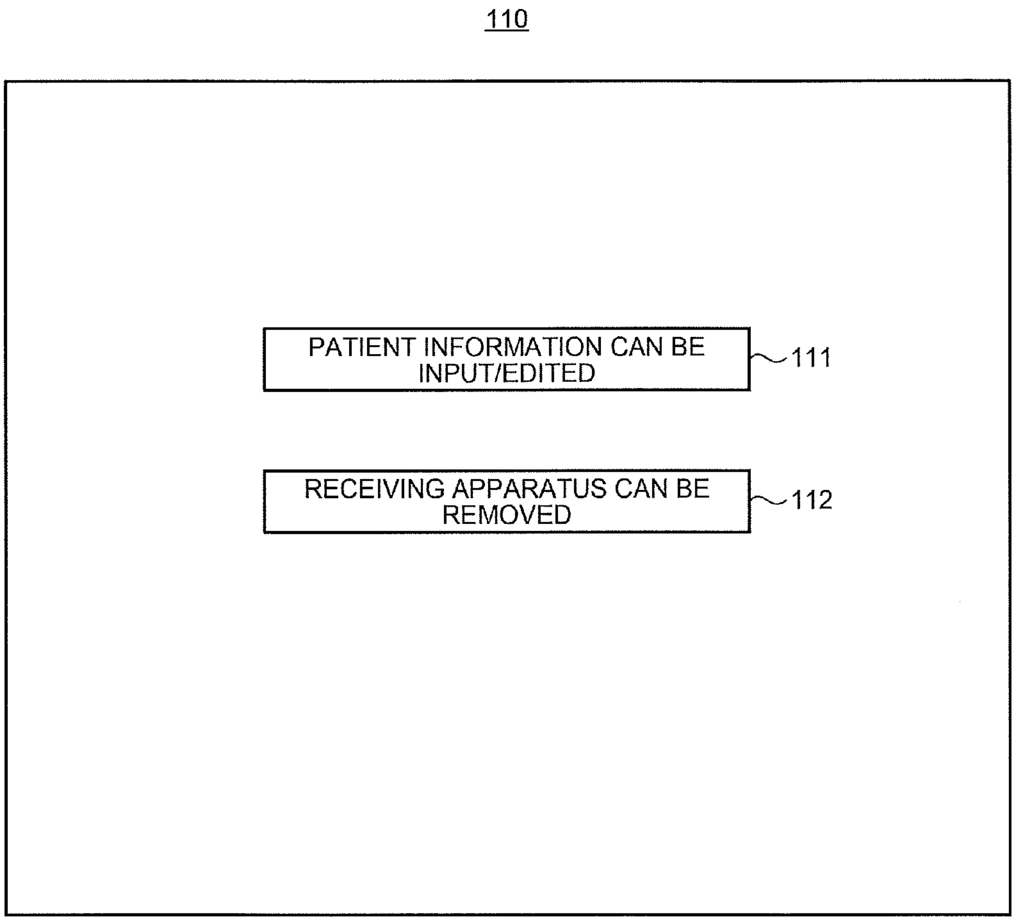
FIG. 7 is a schematic diagram illustrating one example of a transfer completion screen displayed on a display unit after transfer of the in-vivo image data is completed.

In step S103, when the transfer of the in-vivo image data and the like is completed (step S103: Yes), the control unit 60 starts initializing the memory of the receiving apparatus 3. On the other hand, the display control unit 58 causes the display unit 59 to display a transfer completion screen 110 including a message 111 that it is possible to perform various kinds of operations or processing such as an input or an edit of patient information. Next, after the memory is initialized, the display control unit 58 causes the display unit 59 to display a message 112 that the receiving apparatus 3 can be removed from the cradle 5*a*. Here, FIG. 7 illustrates a state where both the messages 111 and 112 are displayed.

After that, in step S105, the control unit 60 causes the image processing unit 53 to start image processing and concurrently causes the position estimating unit 54 to start position estimation processing. According to this, first, the simple position estimation processing unit 54*a* performs simple position estimation processing.

Figure 8:
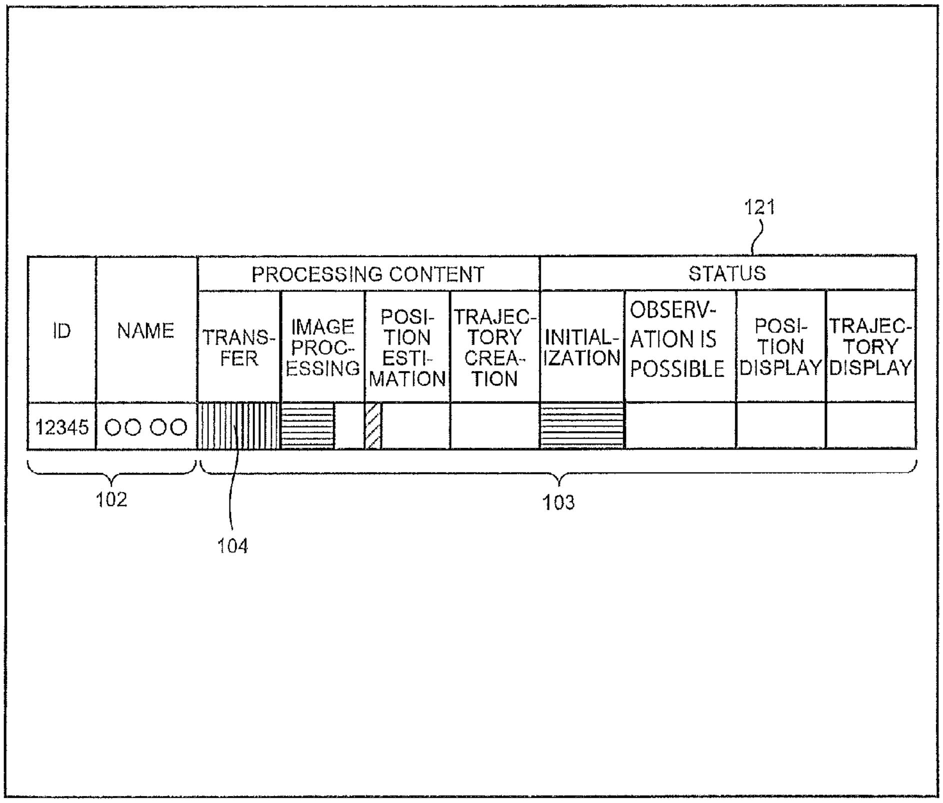
FIG. 8 is a schematic diagram illustrating one example of a processing status display screen displayed on a display unit while performing image processing and trajectory creation processing.

While image processing is performed, for example, as illustrated in FIG. 8, the display control unit 58 causes the display unit 59 to display a processing status display screen 120 indicating the processing status of image processing and trajectory creation processing (step S106). The processing status bar 121 illustrated in FIG. 8 shows that approximately 60% of the image processing is completed and approximately 15% of the position estimation processing is completed. In a case where image processing for a series of in-vivo image data is not completed (step S107: No), the flow proceeds back to S105 to repeat processing and this display is updated.

Figure 9:
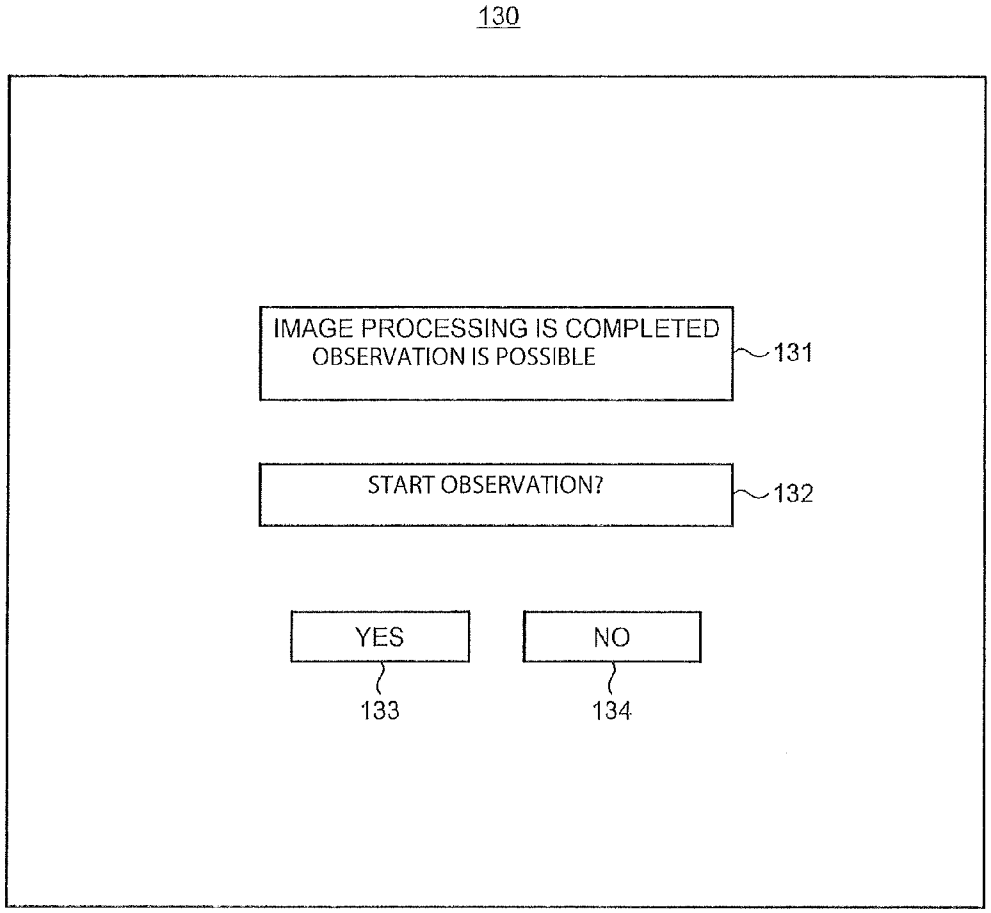
FIG. 9 is a schematic diagram illustrating one example of an observation-possible report screen displayed on a display unit after completion of image processing.

When the image processing for a series of in-vivo image data is completed (step S107: Yes), since the image processing apparatus 5 becomes a state where it is possible to display an in-vivo image, as shown on an observation-possible report screen 130 illustrated in FIG. 9 for example, the display control unit 58 causes the display unit 59 to display a message 131 that a observation is possible (step S108). At this time, to attract user's attention, the display control unit 58 may display the message 131 in a blinking manner. Next, the display control unit 58 causes the display unit 59 to display a message 132 for allowing the user to select whether to start an observation, and selection buttons ("Yes" button 133 and "No" button 134). At this time, when the user selects the "Yes" button 133 by a pointer operation on the screen using a touch panel or a mouse, the display control unit 58 controls the display unit 59 so as to shift to an observation screen. By contrast, when the user selects the "No" button 134, the display control unit 58 causes the display unit 59 to display the processing status bar 121 illustrated in FIG. 8 again. Here, it may be possible to control the display unit 59 to automatically shift to the observation screen after predetermined time from the start of the display of the message 131 has passed without causing the display unit 59 to display the message 132 and the selection buttons.

Figure 10:
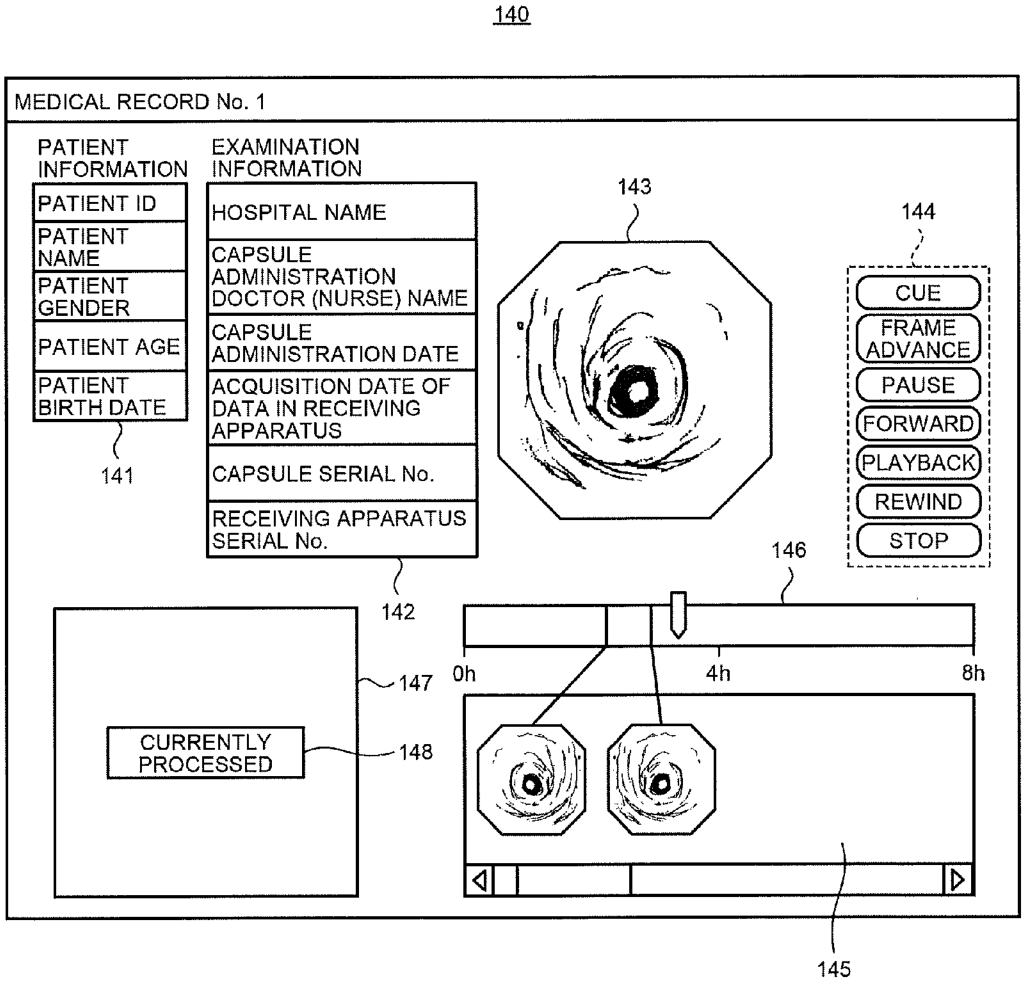
FIG. 10 is a schematic diagram illustrating one example of a observation screen displayed on a display unit while performing position estimation processing.

In step S109, the control unit 60 causes the display unit 59 to display an observation screen and concurrently causes the position estimating unit 54 to perform position estimation processing. According to this, the display control unit 58 controls the display unit 59 so as to display an observation screen 140 as illustrated in FIG. 10, for example. Also, the simple position estimation processing unit 54*a* performs simple position estimation processing in background. This processing continues until the simple position estimation processing is completed (step S110: No, S109).

FIG. 10 is a schematic diagram illustrating a display example of an observation screen. The observation screen 140 illustrated in FIG. 10 includes a patient information area 141 for displaying identification information of the subject 10 that is a patient, an examination information area 142 for displaying identification information of the examination conducted for the subject 10, a main display area 143 for playing back a series of in-vivo images, a playback operation button group 144 for performing a playback operation of an in-vivo image displayed on the main display area 143, a thumbnail area 145 for thumbnailing reduced images of multiple in-vivo images, a time bar 146 indicating the time when an in-vivo image currently displayed on the main display area 143 is obtained, and a trajectory display area 147. Also, on the observation screen 140, the reduced images in the thumbnail area 145 and points on the time bar 146 indicating the time when these reduced images are obtained are connected and displayed.

Figure 11:
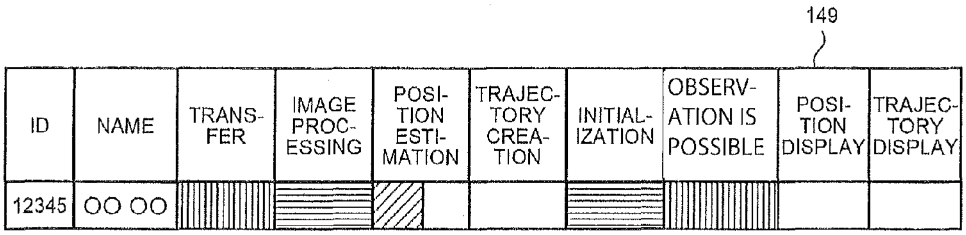
FIG. 11 is a schematic diagram illustrating one example of a processing status bar showing that the position estimation processing is being performed.

The trajectory display area 147 is an area for displaying the trajectory of the capsule endoscope 2 obtained by trajectory creation processing. However, in the stage illustrated in FIG. 10, since information that can be displayed in the trajectory display area 147 is not generated yet, as illustrated in FIG. 10, a message 148 of "currently processed" is displayed. At this time, for example, the processing status bar 149 illustrated in FIG. 11 may be superposed and displayed on the observation screen 140. The processing status bar 149 shows that: 100% of the image processing is completed and an observation is possible; and the position estimation processing is currently performed (approximately 50% completed).

Figure 12:
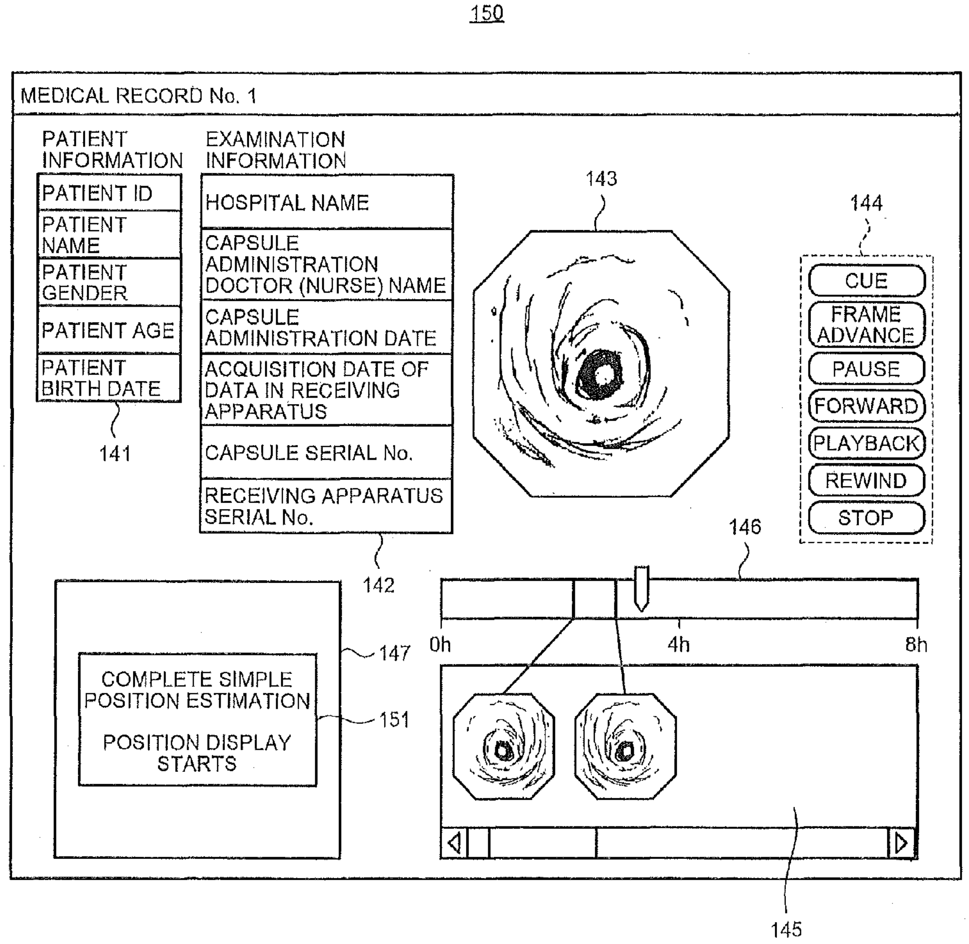
FIG. 12 is a schematic diagram illustrating one example of a observation screen displayed on a display unit when simple position estimation processing is completed.

When the simple position estimation processing is completed (step S110: Yes), for example, as shown on an observation screen 150 of FIG. 12 for example, the display control unit 58 causes the display unit 59 to display a message 151 that a position display of in-vivo images starts (step S111). At this time, the display control unit 58 may display the message 151 in a blinking manner.

In subsequent step S112, the display control unit 58 starts a simple position display of in-vivo images on an observation screen. Also, the control unit 60 causes the detailed position estimation processing unit 54*b* to perform detailed position estimation processing in parallel. This processing continues until the detailed position estimation processing is completed (step S113: No, S112).

Figure 13:
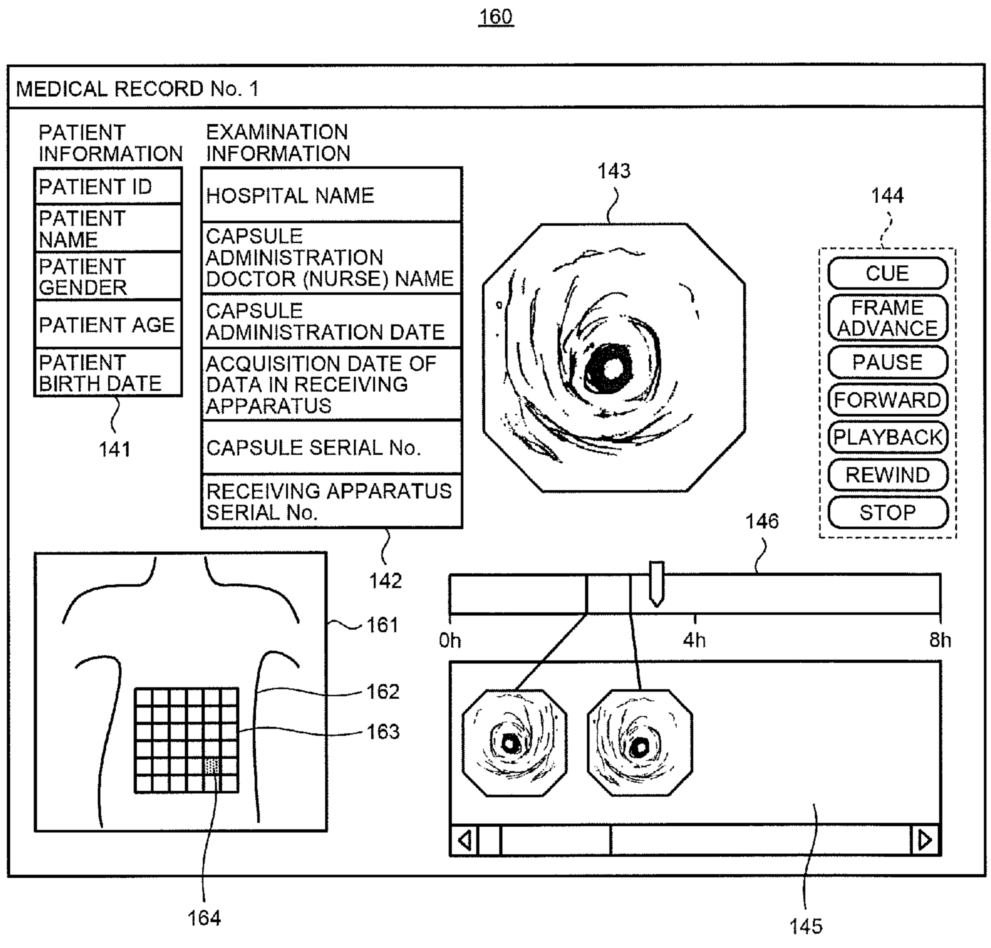
FIG. 13 is a schematic diagram illustrating one example of a observation screen on which a simple position display is made.

FIG. 13 is a schematic diagram illustrating one example of an observation screen on which a simple position display is made. When an observation screen 160 illustrated in FIG. 13 is displayed, first, the display control unit 58 controls the display unit 59 so as to display a human-shaped image 162 representing the subject 10 on a trajectory display area 161. This human-shaped image 162 corresponds to the subject 10 and, for example, a plurality of areas (divided areas) 163 divided in a 6×6 matrix form are displayed thereon. Here, the size of the divided areas 163 is set according to, for example, the sampling density in position estimation processing. Next, from the estimation position information stored in the storage unit 57, the display control unit 58 extracts estimation position information corresponding to time information associated with the in-vivo image currently displayed on the main display area 143. Further, the display control unit 58 controls the display unit 59 so as to display a position display mark 164 on the divided area 163 corresponding to the extracted estimation position information. To attract user's attention, this position display mark 164 may be displayed with high brightness, in a blinking manner or in a predetermined color. By referring to the position display mark 164 and the divided areas 163, the user can roughly recognize a position of an in-vivo image displayed on the main display area 143.

Figure 14:
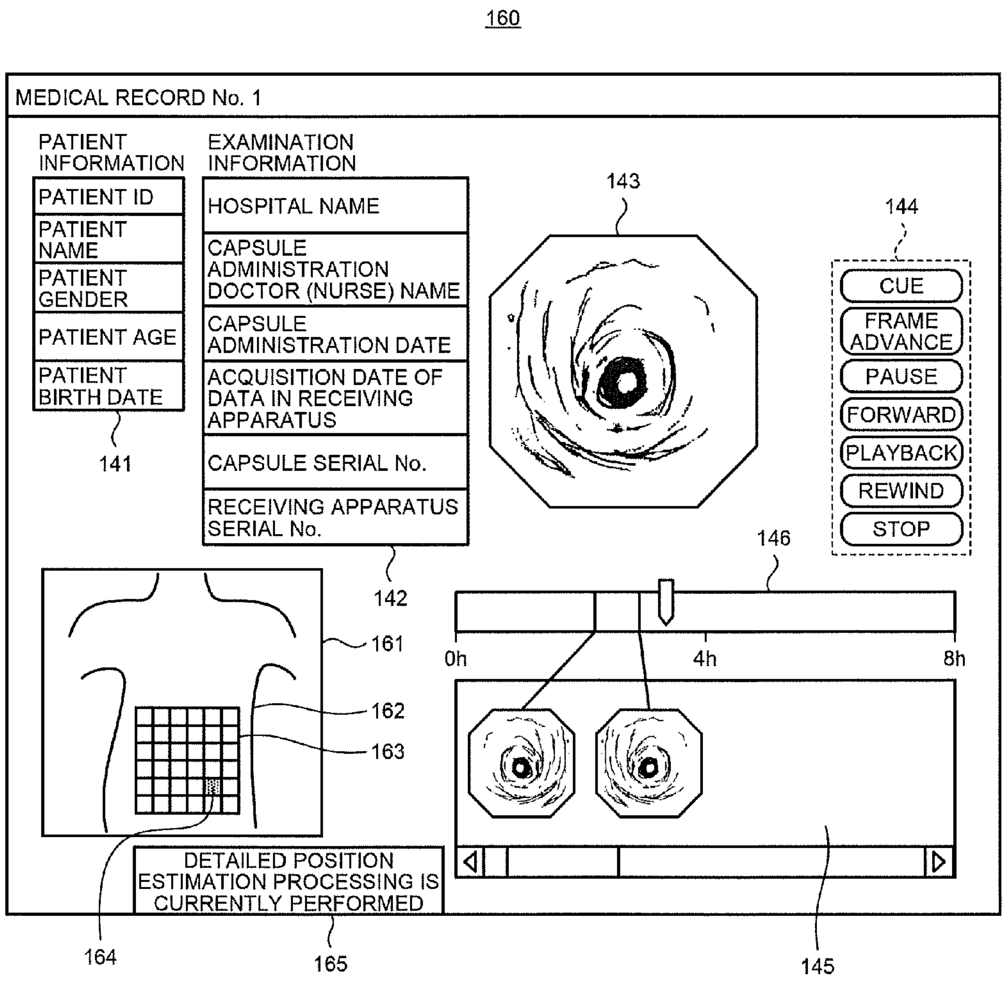
FIG. 14 is a schematic diagram illustrating one example of a observation screen displayed on a display unit while detailed position estimation processing is performed.

Also, at this time, as illustrated in FIG. 14 for example, the display control unit 58 may control the display unit 59 so as to display, on the observation screen 160, a message 165 that the detailed position estimation processing is being performed. Alternatively, the display control unit 58 may superpose and display, for example, the processing status bar 149 illustrated in FIG. 11 on the observation screen 160.

Figure 15:
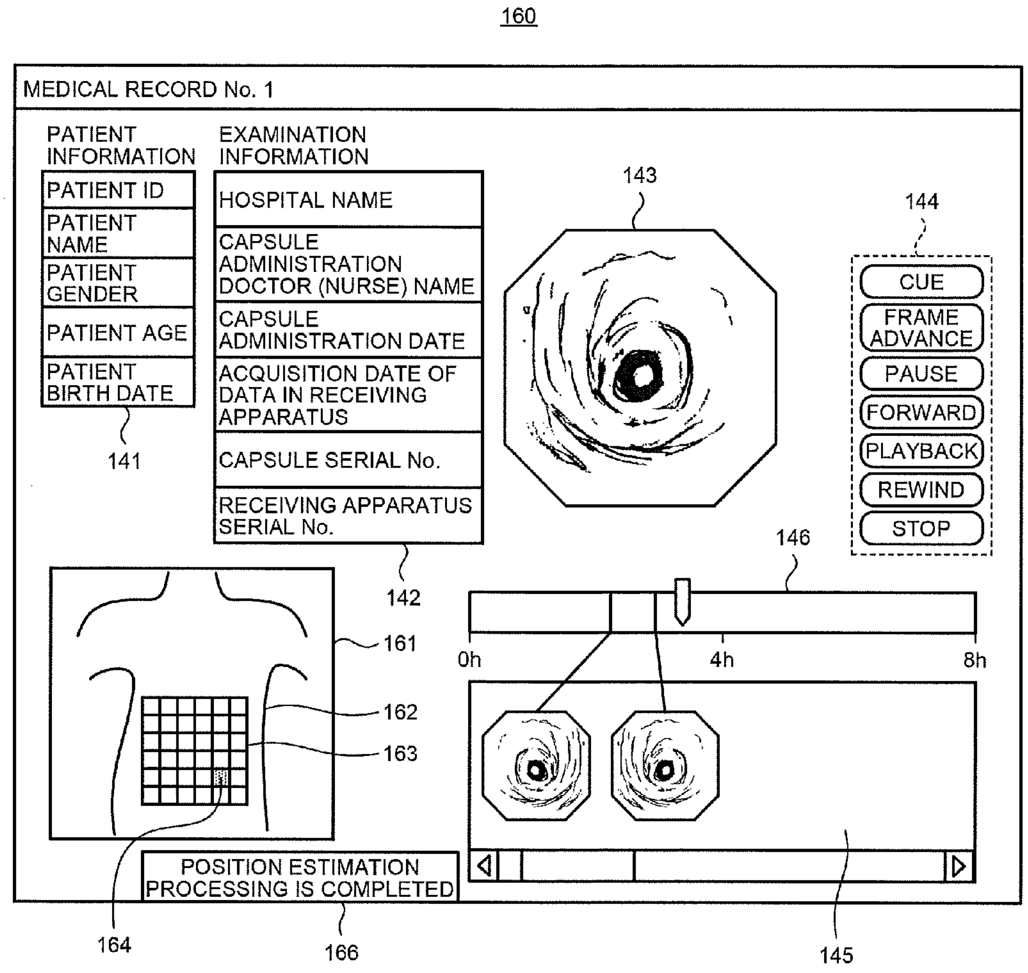
FIG. 15 is a schematic diagram illustrating one example of a observation screen displayed on a display unit when the detailed position estimation processing is completed.

When the detailed position estimation processing is completed (step S113: Yes), as illustrated in FIG. 15 for example, the display control unit 58 controls the display unit 59 so as to display, on the observation screen 160, a message 166 that the position estimation processing is completed (step S114). At this time, the display control unit 58 may display the message 166 in a blinking manner.

In subsequent step S115, the display control unit 58 starts a detailed position display of an in-vivo image on the observation screen. Also, in parallel with this, the control unit 60 causes the trajectory creating unit 55 to perform trajectory creation processing based on a processing result of the detailed position estimation processing. The processing continues until the trajectory creation processing is completed (step S116: No, S115).

Figure 16:
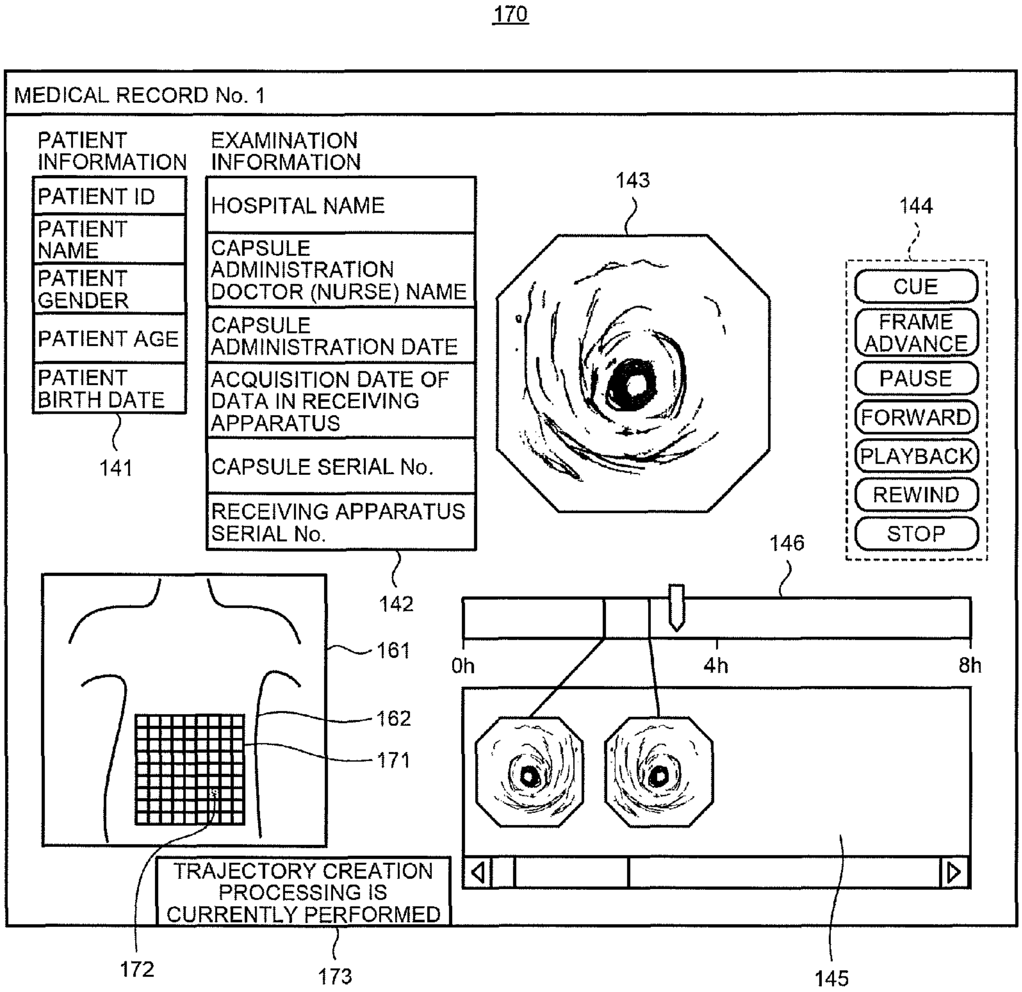
FIG. 16 is a schematic diagram illustrating one example of a observation screen on which a detailed position display is made.

FIG. 16 is a schematic diagram illustrating one example of an observation screen on which a detailed position display is made. In an observation screen 170 illustrated in FIG. 16, divided areas 171 displayed on the human-shaped image 162 have, for example, a 9×9 matrix and are denser than those displayed at the time of simple position display (see FIG. 13). That is, compared to the case of the simple position display, a display specifying a position in more detail is possible. In such the divided areas 171, a position display mark 172 is displayed on a divided area corresponding to the estimation position information of the in-vivo image currently displayed on the main display area 143. Here, at this time, it may be possible to display a message 173 that the trajectory creation processing is being performed, on the observation screen 170.

Figures 17, 18:
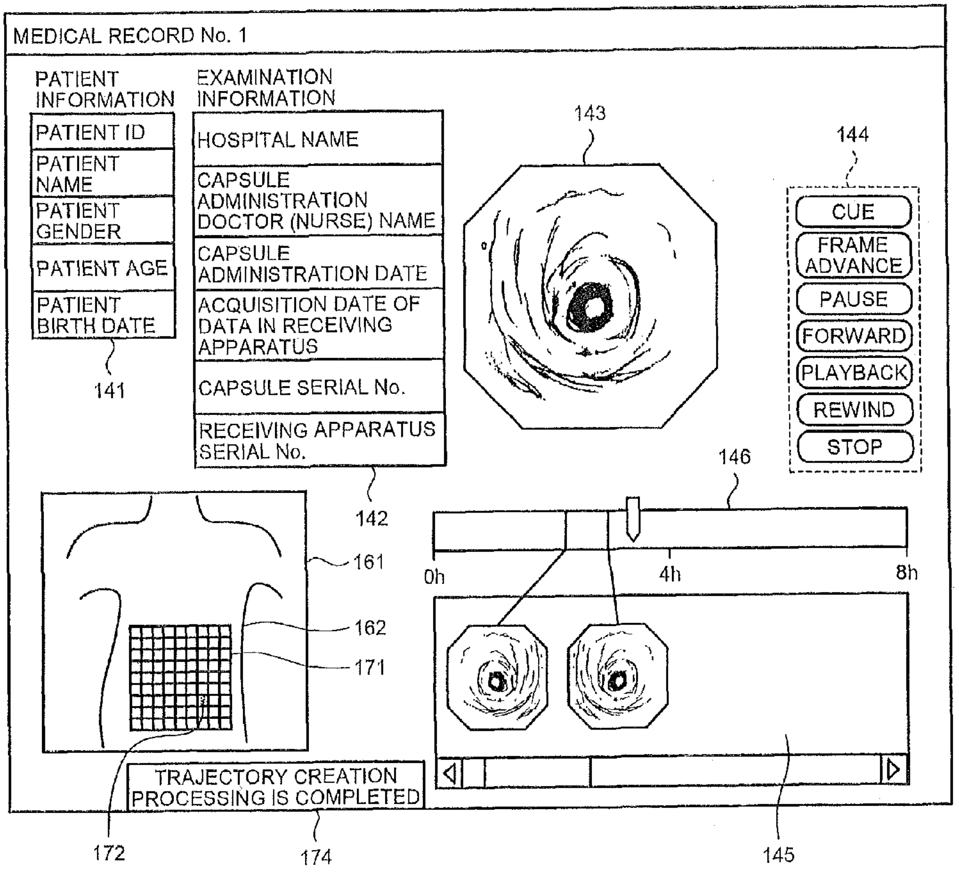
FIG. 17 is a schematic diagram illustrating one example of a observation screen displayed on a display unit when the trajectory creation processing is completed.
FIG. 18 is a schematic diagram illustrating one example of a processing status bar showing that a trajectory display is possible.

When the trajectory creation processing is completed (step S116: Yes), as illustrated in FIG. 17 for example, the display control unit 58 controls the display unit 59 so as to display a message 174 that the trajectory creation processing is completed, on the observation screen 170 (step S117). Also, at this time, the display control unit 58 may superpose and display a processing status bar 175 as illustrated in, for example, FIG. 18, on the observation screen 170. The processing status bar 175 shows that 100% of the trajectory creation processing is completed and a trajectory display is possible.

Figure 19:
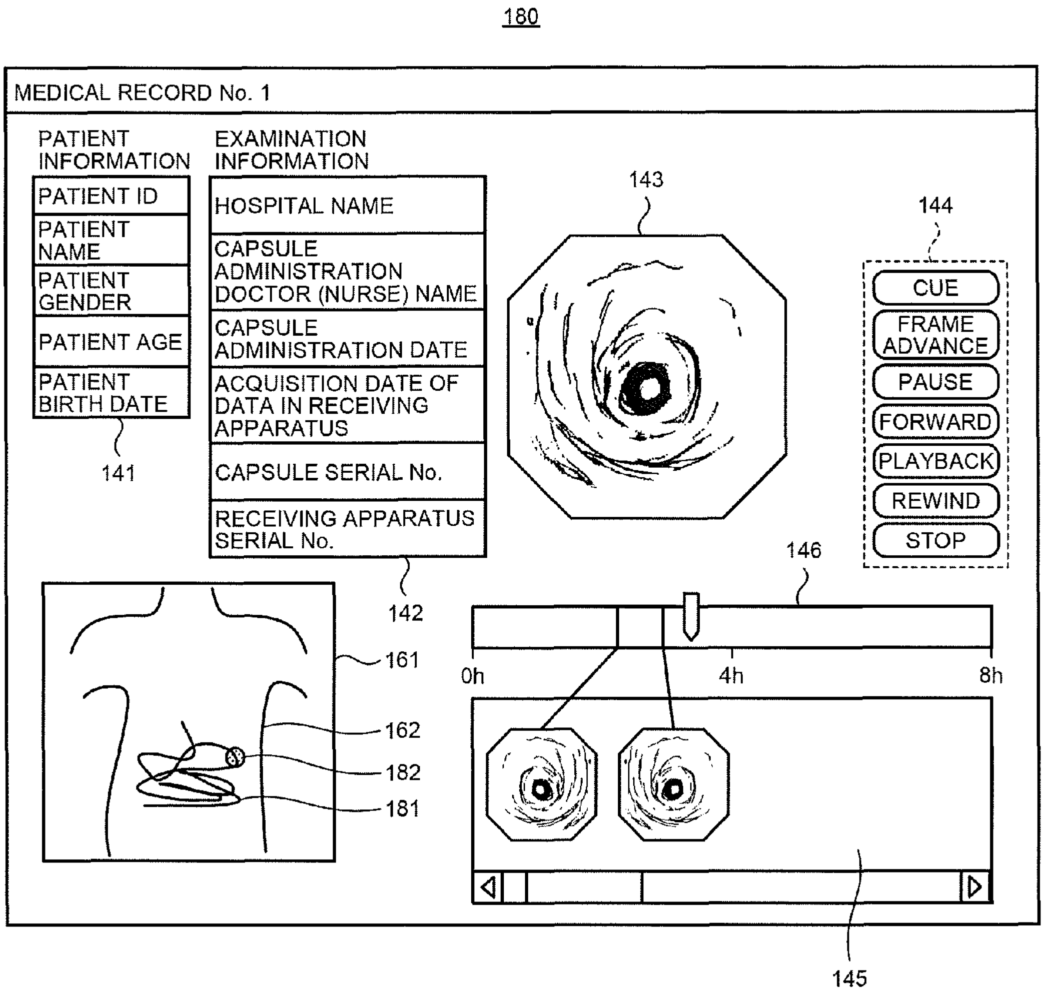
FIG. 19 is a schematic diagram illustrating one example of a observation screen on which a trajectory display is made.

In subsequent step S118, the display control unit 58 controls the display unit 59 so as to display the trajectory created by the trajectory creating unit 55 on the observation screen. FIG. 19 is a schematic diagram illustrating one example of an observation screen on which a trajectory display is made. When an observation screen 180 as illustrated in FIG. 19 is displayed, the display control unit 58 controls the display unit 59 so as to draw and display a trajectory 181 over the human-shaped image 162 displayed on the trajectory display area 161 and further mark, on the trajectory 181, a position of the in-vivo image currently displayed on the main display area 143. To attract user's attention, this position display mark 182 may be displayed with high brightness, in a blinking manner or in a predetermined color.

As described above, according to the present embodiment, since image processing for in-vivo image data and trajectory creation processing of a capsule endoscope are performed in parallel and information that an observation is possible is reported to the user on the stage where the image processing is completed, the user can start an observation early without waiting for a completion of the trajectory creation processing.

To be more specific, according to the present embodiment, since image processing and position estimation processing are performed in parallel after in-vivo image data is transferred from a receiving apparatus to an image display apparatus, it is possible to reduce the time required for processing in total. Also, when the image processing is completed and an observation is possible, since information that the observation is possible is reported to the user to display an observation screen on a display unit while position estimation processing and trajectory creation processing are performed in background, the user can start an observation early. That is, since the user can start the observation without waiting for the completion of position estimation processing and trajectory creation processing with large data processing amounts, it is possible to improve efficiency of an examination.

Also, according to the present embodiment, even before position estimation processing and trajectory creation processing are completed, a position display on an observation screen is started at the time the first position estimation processing by the simple position estimation processing unit 54*a* is completed; therefore the user can early recognize a rough position of the in-vivo image being subjected to an observation.

Incidentally, in the above embodiment, although the simple position estimation processing unit 54*a* and the detailed position estimation processing unit 54*b* perform position estimation processing in two stages, the position estimation processing may be performed over three or more stages. For example, by performing the first position estimation processing with a low sampling density to start a rough position display on an observation screen and then gradually increasing the sampling density to repeat position estimation processing, the position display accuracy may be gradually improved. By contrast, the position estimation processing may be performed in one stage. Even in this case, before trajectory creation processing is completed, the user can perform an observation in an observation screen on which a position display is made.

Also, in the image processing unit 53, when a feature image area such as a lesion area and a hemorrhagic part are detected, a flag indicating a specific image is attached to an in-vivo image including the lesion area or the hemorrhagic part so that the position estimating unit 54 may preferentially perform position estimation processing on the in-vivo image to which the specific image flag is attached. In this case, if a position display starts at the time the position estimation processing on the specific image is completed, the user can early recognize a rough position or an organ of an in-vivo image including the lesion area and the like.

In the above-described embodiment, although various messages are displayed on a display unit and reported to the user, it may be reported to the user in other methods than the display such as the voice reading of messages or in a combination of the display and other methods.

Also, in the above-described embodiment, although data processing related to one patient (subject) has been described, data processing related to a plurality of patients may be performed in parallel. To be more specific, the cradles 5*a* illustrated in FIG. 1 may be connected to the image display apparatus 5 and the receiving apparatuses 3 having completed capturing images by the capsule endoscopes 2 may be sequentially or simultaneously attached to the cradles 5*a*. In this case, for example, like a processing status bar 200 illustrated in FIG. 20, it may be possible to make the display unit 59 list and display processing status of data processing related to a plurality of patients.

Further, in the above-described embodiment, although image recognition processing such as lesion area detection is performed after other image processing (such as density conversion, smoothing and sharping), it is possible to perform the image recognition processing in parallel with other image processing. In this case, it is possible to start a display of an observation screen further earlier.

The above-described embodiment is merely an example to implement the present invention and the present invention is not limited thereto. To add various changes according to a system or the like is within the scope of the present invention. Further, in the scope of the present invention, it is obvious from the above description that other various embodiments are possible.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus that displays an image based on in-vivo image data obtained from a capsule endoscope that captures an in-vivo image of a subject via a receiving apparatus that performs wireless communication with the capsule endoscope, the apparatus comprising:

a storage unit configured to store the in-vivo image data and information that is associated with the in-vivo image data and related to a position of the capsule endoscope in the subject;

an image processing unit configured to perform image processing on the in-vivo image data stored in the storage unit;

a position estimating unit configured to estimate a position of the capsule endoscope in the subject upon capturing the in-vivo image, based on the information related to the position and performs first position estimation processing at a predetermined sampling density for all the position information associated with the in-vivo image data, and, after the first position estimation processing is completed, performs second position estimation processing for all the position information at a higher sampling density than the first position estimation processing;

a display unit configured to display the in-vivo image based on the in-vivo image data on which the image processing is performed in the image processing unit and to display the position of the capsule endoscope estimated by the position estimating unit;

a display control unit configured to control the display unit to display the in-vivo image and to display the position of the capsule endoscope; and a control unit configured to perform image processing in the image processing unit and position estimation processing in the position estimating unit in parallel, wherein when the image processing by the image processing unit is completed and the position estimation processing by the position estimating unit is not completed, the control unit is configured to control the display control unit to display, on the display unit, the in-vivo image based on the in-vivo image data, and information indicating that the position estimation processing is currently performed, and is configured to cause the position estimating unit to perform the position estimation processing concurrently with displaying the in-vivo image;

the display control unit causes the display unit to display the position of the capsule endoscope based on a result obtained by the first position estimation processing, when the first position estimation processing is completed; and the display control unit causes the display unit to display a processing status of image processing in the image processing unit and a processing status of position estimation processing in the position estimating unit.

2. The image display apparatus according to claim 1, wherein the display control unit causes the display unit to display information indicating that an observation is possible, when the image processing by the image processing unit for all the in-vivo image data is completed.

3. The image display apparatus according to claim 1, wherein the display control unit causes the display unit to display information indicating that a position display is possible, when the position estimation processing in the position estimating unit is completed.

4. The image display apparatus according to claim 1, wherein the display control unit causes the display unit to display information indicating that a position display is possible, when the first position estimation processing in the position estimating unit is completed.

5. The image display apparatus according to claim 1, wherein the information related to the position is reception strength information at the time when the receiving apparatus receives the in-vivo image data from the capsule endoscope.

6. The image display apparatus according to claim 1, wherein:

the display unit displays the in-vivo image and displays position information based on a result obtained by the first position estimation processing in the position estimating unit; and the control unit causes the position estimating unit to perform the second position estimation processing while the position information based on the result obtained by the first position estimation processing is displayed on the display unit.

7. An image display apparatus that displays an image based on in-vivo image data obtained from a capsule endoscope that captures an in-vivo image of a subject via a receiving apparatus that performs wireless communication with the capsule endoscope, the image display apparatus comprising:

a storage unit configured to store the in-vivo image data and information that is associated with the in-vivo image data and related to a position of the capsule endoscope in the subject;

an image processing unit configured to perform image processing on the in-vivo image data stored in the storage unit;

a position estimating unit configured to estimate a position of the capsule endoscope in the subject upon capturing the in-vivo image, based on the information related to the position;

a display unit configured to display the in-vivo image based on the in-vivo image data on which the image processing is performed in the image processing unit and to display the position of the capsule endoscope estimated by the position estimating unit;

a display control unit configured to control the display unit to display the in-vivo image and to display the position of the capsule endoscope;

a control unit configured to perform image processing in the image processing unit and position estimation processing in the position estimating unit in parallel; and a trajectory creating unit configured to create a trajectory of the capsule endoscope moving in a biological body, based on the position estimated by the position estimating unit, wherein when the image processing by the image processing unit is completed and the position estimation processing by the position estimating unit is not completed, the control unit is configured to control the display control unit to display, on the display unit, the in-vivo image based on the in-vivo image data, and information indicating that the position estimation processing is currently performed, and is configured to cause the position estimating unit to perform the position estimation processing concurrently with displaying the in-vivo image, and the control unit causes the display unit to display the position estimated by the position estimating unit before trajectory creation processing in the trajectory creating unit is completed.

8. A capsule endoscope system comprising:

a capsule endoscope that is inserted in a subject body to capture an image and generates in-vivo image data indicating an in-vivo image of the subject;

a receiving apparatus that receives the in-vivo image data generated by the capsule endoscope by wireless communication; and an image display apparatus that displays an image based on the in-vivo image data obtained via the receiving apparatus, wherein the image display apparatus comprises:

a storage unit configured to store the in-vivo image data and information that is associated with the in-vivo image data and related to a position of the capsule endoscope in the subject;

an image processing unit configured to perform image processing on the in-vivo image data stored in the storage unit;

a position estimating unit configured to estimate a position of the capsule endoscope in the subject upon capturing the in-vivo image, based on the information related to the position and performs first position estimation processing at a predetermined sampling density for all the position information associated with the in-vivo image data, and, after the first position estimation processing is completed, performs second position estimation processing for all the position information at a higher sampling density than the first position estimation processing;

a display unit configured to display the in-vivo image based on the in-vivo image data on which the image processing is performed in the image processing unit and to display the position of the capsule endoscope estimated by the position estimating unit;

a display control unit configured to control the display unit to display the in-vivo image and to display the position of the capsule endoscope; and a control unit configured to perform image processing in the image processing unit and position estimation processing in the position estimating unit in parallel, wherein when the image processing by the image processing unit is completed and the position estimation processing by the position estimating unit is not competed, the control unit is configured to control the display control unit to display, on the display unit, the in-vivo image based on the in-vivo image data, and information indicating that the position estimation processing is currently performed, and is configured to cause the position estimating unit to perform the position estimation processing concurrently with displaying the in-vivo image;

the display control unit causes the display unit to display the position of the capsule endoscope based on a result obtained by the first position estimation processing, when the first position estimation processing is completed; and the display control unit causes the display unit to display a processing status of image processing in the image processing unit and a processing status of position estimation processing in the position estimating unit.

9. A capsule endoscope system comprising:

a capsule endoscope that is inserted in a subject body to capture an image and generates in-vivo image data indicating an in-vivo image of the subject;

a receiving apparatus that receives the in-vivo image data generated by the capsule endoscope by wireless communication; and an image display apparatus that displays an image based on in-vivo image data obtained from a capsule endoscope that captures an in-vivo image of a subject via a receiving apparatus that performs wireless communication with the capsule endoscope, the image display apparatus comprising:

a storage unit configured to store the in-vivo image data and information that is associated with the in-vivo image data and related to a position of the capsule endoscope in the subject;

an image processing unit configured to perform image processing on the in-vivo image data stored in the storage unit;

a position estimating unit configured to estimate a position of the capsule endoscope in the subject upon capturing the in-vivo image, based on the information related to the position;

a display unit configured to display the in-vivo image based on the in-vivo image data on which the image processing is performed in the image processing unit and to display the position of the capsule endoscope estimated by the position estimating unit;

a display control unit configured to control the display unit to display the in-vivo image and to display the position of the capsule endoscope;

a control unit configured to perform image processing in the image processing unit and position estimation processing in the position estimating unit in parallel; and a trajectory creating unit configured to create a trajectory of the capsule endoscope moving in a biological body, based on the position estimated by the position estimating unit, wherein when the image processing by the image processing unit is completed and the position estimation processing by the position estimating unit is not completed, the control unit is configured to control the display control unit to display, on the display unit, the in-vivo image based on the in-vivo image data, and information indicating that the position estimation processing is currently performed, and is configured to cause the position estimating unit to perform the position estimation processing concurrently with displaying the in-vivo image, and the control unit causes the display unit to display the position estimated by the position estimating unit before trajectory creation processing in the trajectory creating unit is completed.

* * * * *